(12) United States Patent
Loganathan et al.

(10) Patent No.: US 10,285,830 B2
(45) Date of Patent: May 14, 2019

(54) METHOD OF MANUFACTURING IMPLANTS

(71) Applicants: STRYKER CORPORATION, Kalamazoo, MI (US); STRYKER EUROPEAN HOLDINGS I, LLC, Kalamazoo, MI (US)

(72) Inventors: Siddharth Loganathan, Santa Clara, CA (US); Stephen Porter, Piedmont, CA (US)

(73) Assignees: STRYKER CORPORATION, Kalamazoo, MI (US); STRYKER EUROPEAN HOLDINGS I, LLC, Kalamazoo, MI (US)

( * ) Notice: Subject to any disclaimer, the term of this patent is extended or adjusted under 35 U.S.C. 154(b) by 455 days.

(21) Appl. No.: 14/948,919

(22) Filed: Nov. 23, 2015

(65) Prior Publication Data
US 2016/0158036 A1 Jun. 9, 2016

Related U.S. Application Data

(60) Provisional application No. 62/087,962, filed on Dec. 5, 2014.

(51) Int. Cl.
*B23K 26/38* (2014.01)
*A61F 2/844* (2013.01)
(Continued)

(52) U.S. Cl.
CPC ............. *A61F 2/844* (2013.01); *A61F 2/89* (2013.01); *B23K 26/38* (2013.01); *A61F 2/915* (2013.01);
(Continued)

(58) Field of Classification Search
CPC .. A61F 2/844; A61F 2/89; A61F 2/915; A61F 2/966; A61F 2002/91541;
(Continued)

(56) References Cited

U.S. PATENT DOCUMENTS 3,454,695 A * 7/1969 Holmgren ............. B29C 53/083
264/209.3
4,619,274 A 10/1986 Morrison
(Continued)

OTHER PUBLICATIONS

PCT International Search Report and Written Opinion for International Patent Application No. PCT/US2015/062135, Applicant Stryker Corporation, filed on May 19, 2016 (14 pages).
(Continued)

*Primary Examiner* — Tu B Hoang
*Assistant Examiner* — Masahiko Muranami
(74) *Attorney, Agent, or Firm* — Vista IP Law Group LLP

(57) ABSTRACT

A method of manufacturing a tubular medical implant, such as a stent, includes introducing a liquid polymer material into an axial lumen of an elongate metal tube, the metal tube having an inner wall defining the lumen; allowing the polymer material to solidify within the metal tube lumen, the solidified polymer forming a high friction surface in contact with the inner wall of the metal tube; securing the metal tube, including the solidified polymer material therein, to a collet of a laser etching system; and laser etching a predetermined pattern of openings in the metal tube.

5 Claims, 20 Drawing Sheets

(51) Int. Cl.
    *A61F 2/89*   (2013.01)
    *A61F 2/915*  (2013.01)
    *A61F 2/966*  (2013.01)
    *B23K 101/06* (2006.01)

(52) U.S. Cl.
    CPC ..... *A61F 2/966* (2013.01); *A61F 2002/91541* (2013.01); *A61F 2002/91575* (2013.01); *A61F 2240/002* (2013.01); *B23K 2101/06* (2018.08)

(58) Field of Classification Search
    CPC ..... A61F 2002/91575; A61F 2240/002; B23K 26/38; B23K 26/384; B23K 37/0538; B28B 7/28; B28B 7/34
    USPC ....... 219/121.69, 121.68, 59.1, 61, 61.1, 66; 427/2.1; 264/334, 338; 623/1.15; 83/15, 83/21, 25
    See application file for complete search history.

(56) References Cited

U.S. PATENT DOCUMENTS

| | | |
|---|---|---|
| 5,780,807 A | 7/1998 | Saunders |
| 5,906,759 A | 5/1999 | Richter |
| 5,922,005 A | 7/1999 | Richter et al. |
| 6,563,080 B2 | 5/2003 | Shapovalov et al. |
| 2003/0055378 A1* | 3/2003 | Wang ..................... A61F 2/958 604/103.07 |
| 2004/0079737 A1* | 4/2004 | Pinchasik ................ A61F 2/91 219/121.64 |
| 2009/0008086 A1* | 1/2009 | Ehlinger ............. E21B 17/1021 166/241.6 |
| 2010/0193485 A1* | 8/2010 | Anukhin ................ B23K 26/16 219/121.72 |
| 2013/0119586 A1* | 5/2013 | Gale ...................... B29C 71/04 264/400 |
| 2014/0246141 A1* | 9/2014 | Oldroyd ................. B29C 33/02 156/175 |

OTHER PUBLICATIONS

International search report for PCT/US2015/062135, filed Nov. 23, 2015 (dated Mar. 4, 2016) (7 pages).

* cited by examiner

METHOD OF MANUFACTURING IMPLANTS

RELATED APPLICATION DATA

The present application claims the benefit under 35 U.S.C. § 119 to U.S. provisional patent application Ser. No. 62/087,962, filed Dec. 5, 2014. The foregoing application is hereby incorporated by reference into the present application in its entirety.

FIELD

The present disclosure relates generally to medical devices such as medical implants. More particularly, the present disclosure pertains to methods of manufacturing medical implants by cutting tubes.

BACKGROUND

Medical devices such as stents, stent grafts, and vena cava filters, collectively referred to hereinafter as "stents," are often utilized for treating various types of disease of tubular organs having lumens. A medical prosthesis, such as a stent for example, may be loaded onto a stent delivery device and then introduced into a tubular organ lumen in a delivery configuration having a reduced diameter. Once delivered to a target location within the body, the stent may then expand or be expanded to an expanded configuration within the tubular organ to support and reinforce the organ wall while maintaining the tubular organ in a patent, unobstructed condition. Stents can be used to treat intracranial aneurysms, which can rupture and are a major cause of stroke. When implanted in vessel at the site of an aneurysm, a stent reinforces the vessel and reduces the probability of rupture. Stents can also be used to treat atherosclerosis, in which the diameter of an artery is narrowed by a buildup of plaque on the artery walls. When implanted in an atherosclerotic artery, a stent reinforces the artery and reduces restenosis following angioplasty to open the narrowed artery. Further, Stents can be used in other tubular organs with anatomical lumens, such as bile ducts and ureters. Moreover, Stents can be used to expand a segment of a tubular organ.

Stents are generally tubular devices for insertion into body lumens. However, it should be noted that stents may be provided in a wide variety of sizes and shapes. Balloon expandable stents require mounting over a balloon, positioning, and inflation of the balloon to expand the stent radially outward. Self-expanding stents expand into place when unconstrained, without requiring assistance from a balloon. A self-expanding stent may be biased so as to expand upon release from the delivery catheter and/or include a shape-memory component which allows the stent to expand upon exposure to a predetermined condition. Self-expanding stents are biased to an expanded configuration. Some stents may be characterized as hybrid stents which have some characteristics of both self-expandable and balloon expandable stents.

Typically, a stent is implanted in a blood vessel or other body lumen at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the stent is caused or allowed to expand to a predetermined diameter in the vessel. Many delivery devices include sheaths or catheters, and delivery members having bumpers thereon to push and pull stents through the sheaths and catheters. A catheter may be configured to be bent without breaking while navigating through tortuous vasculature.

Stents can be made from a variety of materials, including polymers (e.g., nonbioerodable and bioerodable plastics) and metals. Bioerodable polymer stents are desirable for some applications due to their biodegradability and generally increased flexibility compared to metal stents. Stents can be made from shape memory materials, such as shape memory metals (e.g., Nitinol) and polymers (e.g., polyurethane). Such shape memory stents can be induced (e.g., by temperature, electrical or magnetic field or light) to take on a shape (e.g., a radially expanded shape) after delivery to a treatment site. Other stent materials include stainless steel, and Elgiloy. In drug delivery stents, the surface of the stent can be coated with a polymeric carrier, which can include a bioactive or therapeutic agent.

Stents are typically cylindrical scaffolds formed from a set of stent elements (i.e., struts). The struts can interconnect in a repeating pattern or in a random manner. The scaffolding can be woven from wires, cut out of tubes, or cut out of sheets of material that are subsequently rolled into a tube. Tubes and sheets from which stents are cut as also known as stent "preforms." The manner in which a stent's struts interconnect determines its longitudinal and radial rigidity and flexibility. Longitudinal rigidity is needed to expand and maintain a lumen of a tubular organ, but longitudinal flexibility is needed to facilitate delivery of the stent (e.g., through tortuous vasculature). Radial rigidity is also needed to expand and maintain a lumen of a tubular organ, but radial flexibility is needed to facilitate radial compression of a stent for delivery. Stent patterns are typically designed to maintain an optimal balance between longitudinal and radial rigidity and flexibility for the stent.

Stents can be cut from tubes and sheet using a variety of techniques, including laser cutting or etching a pattern onto a tube or sheet to form struts from the remaining material. Lasers cutting or etching may be performed on a sheet, which is then rolled into a tube, or a desired pattern may be directly cut or etched into a tube. Other techniques involve forming a desired pattern into a sheet or a tube by chemical etching or electrical discharge machining. Laser cutting of stents has been described in a number of publications including U.S. Pat. No. 5,780,807 to Saunders, U.S. Pat. Nos. 5,922,005 and 5,906,759 to Richter and U.S. Pat. No. 6,563,080 to Shapovalov, the entire disclosures of which are incorporated herein by reference, as though set forth in full. Stents may also include components that are welded, bonded or otherwise engaged to one another.

Laser cutting a stent from a metal tube typically includes mounting the metal tube onto a mandrel. A "mandrel" is generally a metal rod or bar on which a stent may be shaped or cut. The mandrel provides structural support to the tube as it is being cut and shaped to form the stent. See, e.g., U.S. Pat. No. 5,780,807 to Saunders. However, strut widths are limited in laser cutting of tubes to form stents because tubes supported by known mandrels vibrate (to a certain degree) when impinged upon by a laser. This vibration places a lower limit on the size of struts (and other stent features) that can be consistently cut with a laser. Such known supported tubes can also sag, which would move the focus point of the laser, thereby affecting the cutting of the tubes.

Accordingly, there is an ongoing need for systems for and methods of laser cutting tubes to form stents with fine features such as struts with small widths.

SUMMARY

In one embodiment, a method of manufacturing a tubular medical implant includes introducing a liquid polymer material into an axial lumen of an elongate metal tube, the metal tube having an inner wall defining the lumen, allowing the polymer material to solidify within the metal tube lumen, the solidified polymer forming a high friction surface in contact with the inner wall of the metal tube, securing the metal tube, including the solidified polymer material therein, to a collet of a laser etching system, and laser etching a predetermined pattern of openings in the metal tube.

In a single or multiple embodiments, the method also includes inserting one or more elongate pieces of solid polymer into the metal tube lumen prior to allowing the liquid polymer material to solidify therein. The method may also include removing the solidified polymer material from the metal tube lumen after laser etching the predetermined pattern of openings. The solidified polymer material may be removed using one or more of a solvent, heat, and mechanical energy.

In another embodiment, a method of manufacturing a tubular medical implant includes inserting an elongate polymer or pre-polymer member into an axial lumen of an elongate metal tube, the metal tube having an inner wall defining the axial lumen, radially expanding the polymer member within the metal tube lumen to thereby increase a frictional force applied by the polymer member against the inner wall of the metal tube, securing the metal tube, including the expanded polymer member therein, to a collet of a laser etching system, and laser etching a predetermined pattern of openings in the metal tube.

In a single or multiple embodiments, the polymer member is hollow and defines an axial lumen, and radially expanding the polymer member includes heating the polymer member, and increasing a pressure within the axial lumen of the heated polymer member. In other embodiments, the polymer member is solid, and radially expanding the polymer member includes heating the polymer member, and axially compressing the heated polymer member. The method may also include, after radially expanding the polymer member, and before laser etching the predetermined pattern of openings in the metal tube, annealing the polymer member to reduce or eliminate residual stress stored therein.

In a single or multiple embodiments, the method also includes, after laser etching the predetermined pattern of openings in the metal tube, reheating the polymer member, axially stretching to thereby radially contract the reheated polymer member, and removing the radially contracted polymer member from the axial lumen of the metal tube. The method may also include, prior to inserting the polymer member into the lumen of the metal tube, applying a tie-layer of adhesive material to one or both of the inner wall of the metal tube and an outer surface of the polymer member. Inserting the elongate polymer member into the metal tube lumen may include extruding the polymer member directly into the metal tube lumen.

In still another embodiment, a method of manufacturing a tubular medical implant includes inserting a polymer tube into an axial lumen of a metal tube, the metal tube having an inner wall defining the metal tube lumen, introducing a liquid polymer material into an axial lumen of the polymer tube, allowing the liquid polymer material to solidify within the polymer tube lumen, where an outer surface of the polymer tube forms a high friction surface in contact with the inner wall of the metal tube, securing the metal tube, including the respective polymer tube and solidified polymer material therein, to a collet of a laser etching system, and laser etching a predetermined pattern of openings in the metal tube.

In a single or multiple embodiments, the method also includes inserting one or more elongate pieces of solid polymer into the polymer tube lumen prior to allowing the liquid polymer material to solidify therein. The method may also include, after laser etching the predetermined pattern of openings in the metal tube, removing the solidified polymer material from within the polymer tube lumen, and removing the polymer tube from the metal tube lumen. The solidified polymer may be removed from the polymer tube using one or more of a solvent, heat, and mechanical energy. The polymer tube may be removed from the metal tube lumen by heating the polymer tube, axially stretching to thereby radially contract the heated polymer tube, and removing the radially contracted polymer tube from the metal tube lumen. The method may also include, prior to inserting the polymer tube into the metal tube lumen, applying a tie-layer of adhesive material to one or both of the inner wall of the metal tube and an outer surface of the polymer tube.

In yet another embodiment, a method of manufacturing a tubular medical implant, includes rotating an elongate metal tube, the metal tube having an inner wall defining an axial lumen, introducing a liquid composition including a solvent and a polymer material into the axial lumen of the rotating metal tube to form a tubular polymer layer on the inner wall of the metal tube as the solvent evaporates and the polymer material solidifies, the tubular polymer layer defining an axial lumen, securing the metal tube, including the tubular polymer layer therein, to a collet of a laser etching system, and laser etching a predetermined pattern of openings in the metal tube.

In a single or multiple embodiments, the method also includes heating the tubular polymer layer within the metal tube lumen, and increasing a pressure of the axial lumen of the heated polymer layer to thereby increase a frictional force applied by the tubular polymer layer member against the inner wall of the metal tube. The method may also include, after laser etching the predetermined pattern of openings in the metal tube, removing the tubular polymer layer from the axial lumen of the metal tube using one or more of a solvent, heat, and mechanical energy. The method may also include, after laser etching the predetermined pattern of openings in the metal tube, heating the tubular polymer layer, axially stretching to thereby radially contract the reheated tubular polymer layer, and removing the radially contracted tubular polymer layer from the axial lumen of the metal tube.

Other and further aspects and features of embodiments will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION OF THE ILLUSTRATED EMBODIMENTS

Figure 1:
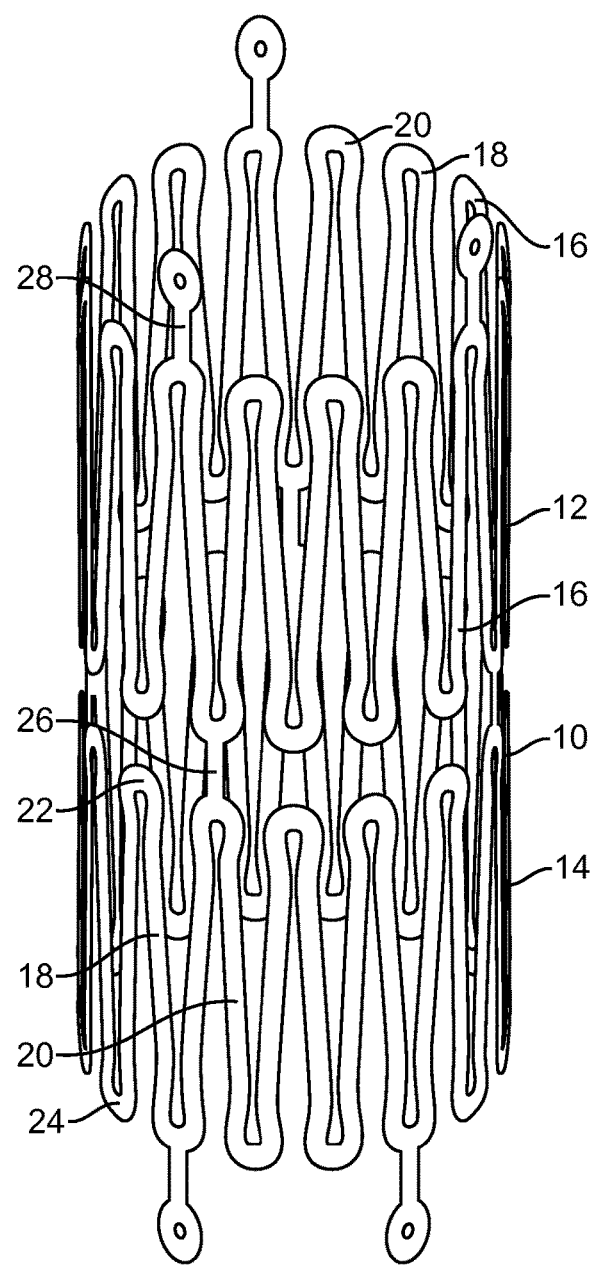
FIG. 1 is a perspective view of portions of a pair of connected expandable members forming a portion of a stent, and shown in a contracted state.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Figure 2:
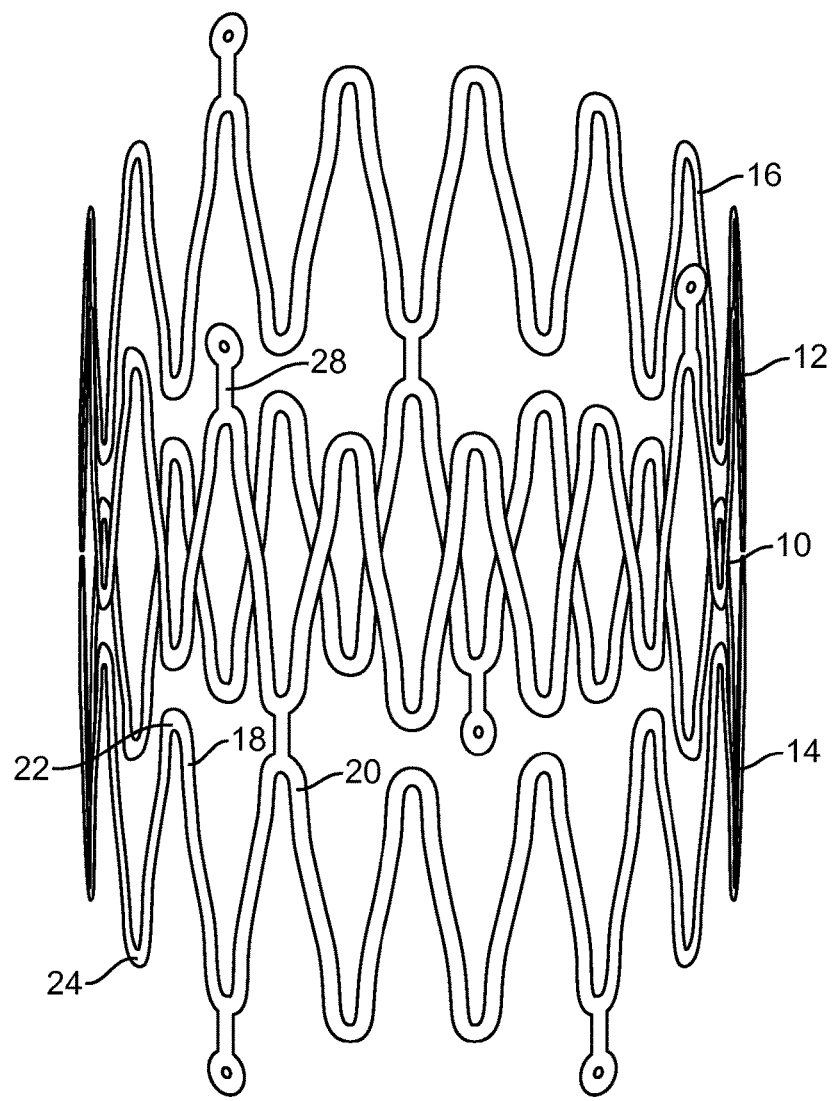
FIG. 2 is a perspective view of the portion of the expandable members depicted in FIG. 1 in an expanded state.

FIGS. 1 and 2 show a portion of a typical stent 10, in the stent's contracted and expanded states, respectively. The stent 10 includes a plurality of expandable members (e.g., rings), such as expandable members 12, 14. In actual construction, the stent 10 may include many such members, e.g., 2-20, collectively forming an elongate cylindrical tube.

Each expandable member 12, 14 of the stent 10 is formed of a continuous elongate element, such as elongate element 16 in member 12, which forms a plurality of wave segments, such as wave segments 18, 20 in member 14. The wave segments have opposite looped peaks, such as looped peaks 22, 24 in wave segment 18.

Adjacent expandable members are connected one to another by axial connectors, such as axial connector 26 joining members 14, 16, and axial connector 28 joining expandable member 12 to a third member (not shown). As seen, the axial connectors 26, 28 connect opposing peaks in adjacent members, although connections to other parts of the wave segments is contemplated. In a typical stent, the connectors are spaced from one another by at least one, and preferably three or four unconnected confronting peaks. That is, a majority of the opposing peaks are unconnected, providing greater stent flexibility in bending away from the stent long axis. Although the connectors shown here are simple linear connectors, the connectors may assume more complicated configurations, such as curved or zig-zag shapes which may themselves stretch to accommodate off-axis bending of the stent, providing greater flexibility.

In one embodiment, the stent has a contracted-state outer diameter (FIG. 1) of between 0.5 mm to 2 mm, more preferably 0.71 mm to 1.65 mm, and a length of between about 0.5 cm to 4 cm, composed of 2 to 20 expandable members, each about 0.25 mm to 1.0 mm in length. The axial connectors have a length typically of 3-20% that of the expandable members.

Each expandable member is composed of between 5-25 wave segments, defined as repeating segments of the associated elongate elements, as described below with respect to FIGS. 3-5. In its expanded state, shown in FIG. 2, the stent diameter is at least twice and up to 8-9 times that of the stent in its contracted state. Thus, a stent with a contracted diameter of between 0.7 mm to 1.5 mm may expand radially to a selected expanded state of between 2 mm to 8 mm or more.

Figure 3:
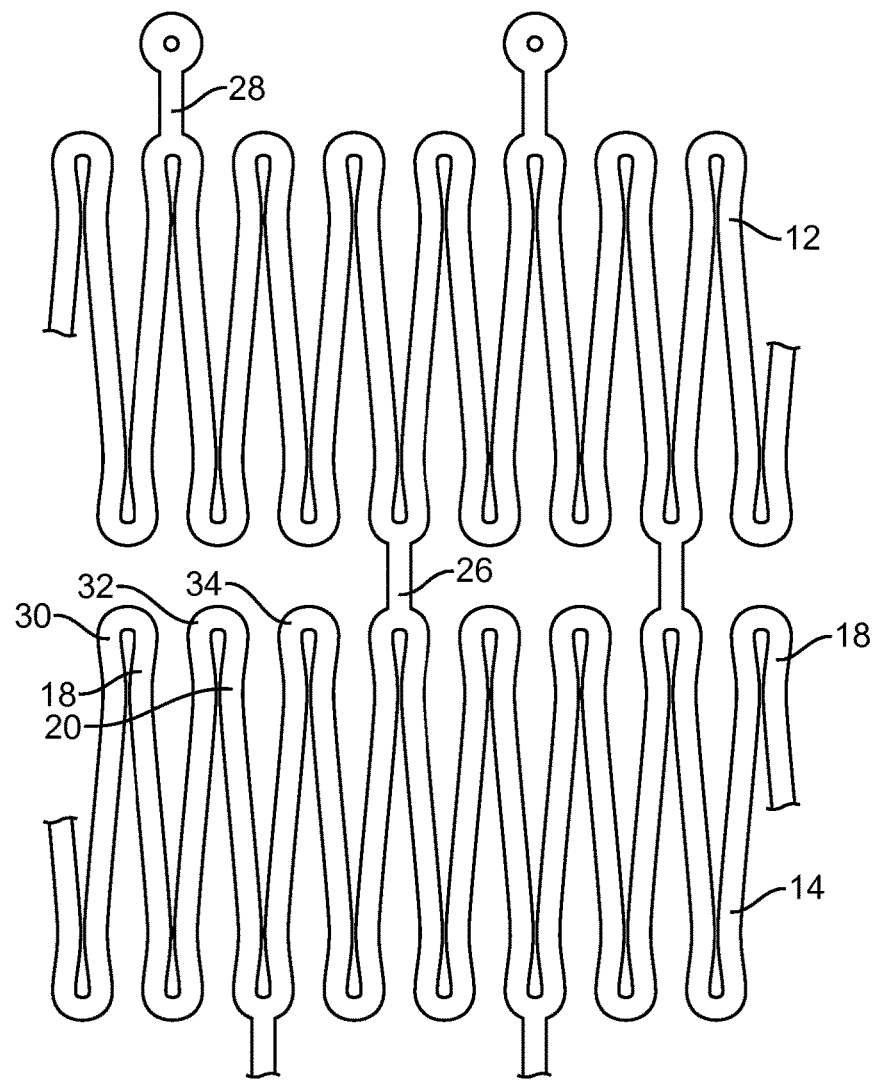
FIG. 3 is a side view of respective portions of the expandable members depicted in FIG. 1, in a contracted state, where the stent has been cut open along its longitudinal axis and laid out in a plane.
Figure 4:
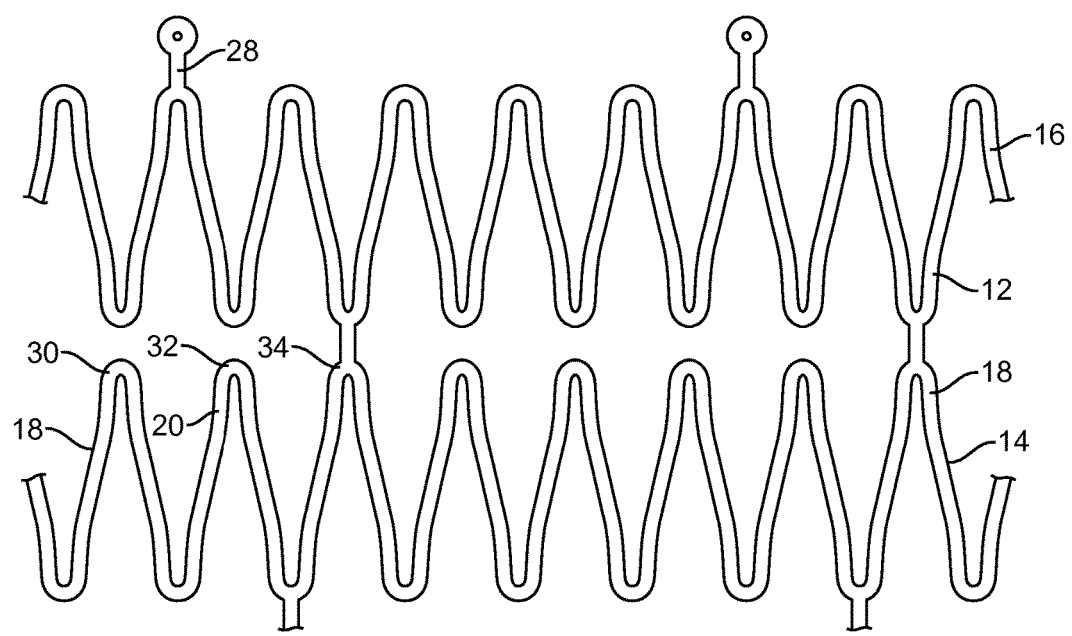
FIG. 4 is a side view of the respective portions of the expandable members depicted in FIG. 3 in an expanded state.
Figure 5:
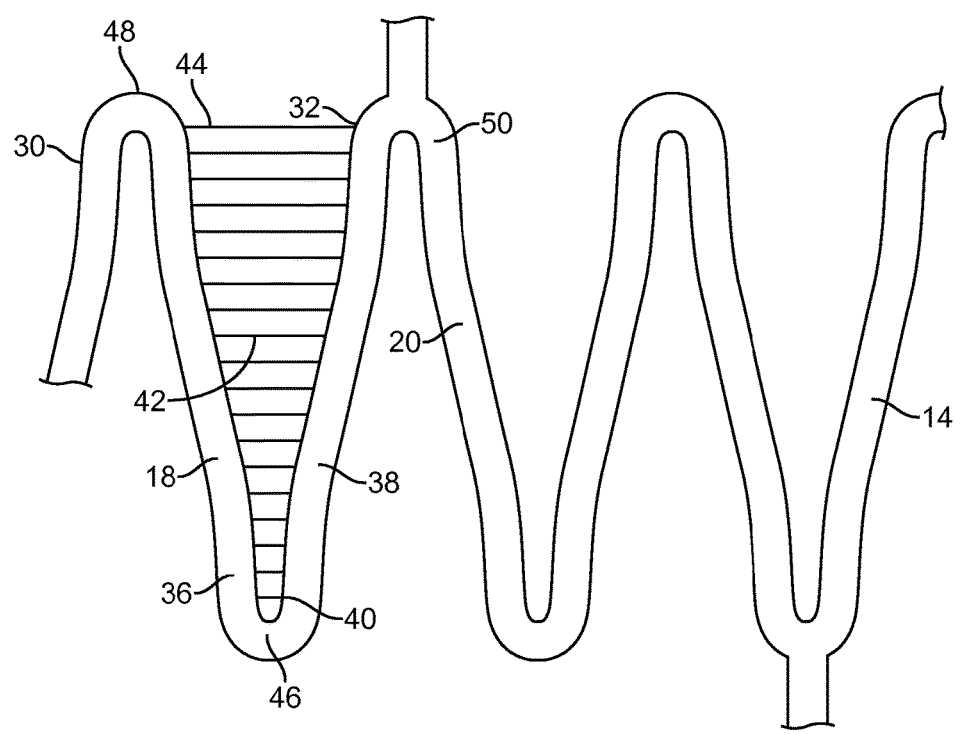
FIG. 5 is a side view of an expandable member depicted in FIG. 4 in an expanded state, illustrating the change in distance between adjacent sides of a wave segment in an expandable member, on proceeding from a lower wave peak to the opposite (upper) side of member.

The relationship between the shape of the wave segments in the expandable members and the mode of radial expansion of the stent 10 is illustrated particularly in FIGS. 3 and 4. FIGS. 3 and 4 show portions of the expandable members with the stent 10 cut open along its longitudinal axis and laid out in a plane or sheet. In particular, the figures show portions of expandable members 12, 14, each formed of a continuous elongate element, such as elongate element 18 forming member 14. Each elongate element, in turn, is formed of a series of repeating-unit wave segments, such as wave segments 18, 20, where the "end" of one segment is the "beginning" of the next segment.

The "end/beginning" point of the wave segments, which occurs at the same phase point in each wave, is arbitrary, and for purposes of illustration is indicated at a point, such as indicated at 30, 32, 34, which is near the top of the loop in the upper looped peak of each wave segment. Thus, wave segment 18 is defined as the portion of the elongate element between points 30, 32, and segment 20, as the portion of the element between points 32, 34.

In the stent's contracted state, the wave segments are compressed closely together, as seen in FIG. 3, where adjacent looped peaks are in contact with one another or nearly in contact, and the looped peaks are squeezed together. The wave segments forming the elongate element accommodate movement of the opposite arms of a wave segment, such as opposite arms 36, 38 in segment 18, away from one another, with relatively larger movement occurring in the center portion of the wave segment, i.e., the portion between opposite looped peaks.

This feature is illustrated particularly in FIG. 5A, which shows three adjacent wave segments, including segment 18 in its expanded (or expanding) form. Distances H between opposite sides 36, 38 of the wave segment 18, such as distances 40, 42, 44, are shown for a number of points between looped peak 46 in segment 18 and opposite looped peaks 48 in segment 18 and 50 in adjacent segment 20. In the plot shown in FIG. 5B, the x-axis represents the distance from a peak in a wave segment to the opposite peak of the wave segment, with the ordinates 40, 42, 44 in FIG. 5A shown. The distance along the y-axis represents the distance between opposite sides of the wave segment. As seen, the plot shows a relatively small slope (Δx/Δy) in the wave regions adjacent the peaks and the greatest slope in the center region of the segment between the looped peaks. The point of greatest slope, corresponding roughly to midpoint 42 between the peaks, is an inflection point in the plot, as the slope of the plot increases between points 40 and 42, and then begins to decrease between points 42 and 44. Further, with reference to FIGS. 1 and 3, the distance between opposite sides of a wave segment in the contracted state is at a minimum at a point intermediate the looped peaks, where opposite sides of a wave appear to be touching in the two figures.

The characteristics of the elongate element shape provide several important advantages in a stent intended for use in a small-diameter site. First, the stent can be forced into a highly compressed or contracted state, (FIGS. 1 and 3) with relatively little bending or stress in the peak regions. This contrasts with a saw-tooth wave, where much of the compression stress is concentrated at the peak points, and also with a regular sine wave that lacks the ability to be compressed tightly due to its relatively wide peak loops. Similarly, the stress on axially connected elongate element peaks that can occur when the stent is bent away from its long axis (during movement through a tortuous vascular path) is distributed over the loop region, rather than being concentrated at a point. Both aspects reduce the possibility of failure of the stent by metal fatigue.

At the same time, the expandable element can undergo a several fold radial expansion by virtue of the ability to be close packed in a contracted state (unlike a sine wave), and still provide significant expansion between wave segment arms. This is in contrast to a sine wave elongate element in which compression at the peaks, and thus the number of wave segments that can be accommodated in the contracted state, is limited.

Finally, and as can be appreciated from FIGS. 3 and 4, radial expansion of the stent produces little change in the overall length of the expandable members (and therefore the stent), preserving the overall stent length during deployment and expansion.

While the stent pattern depicted in FIGS. 1 to 5A is relatively simple, other stent patterns are more complicated. For instance, other stent patterns may include elongate elements having different widths. Examples of such stent patterns are depicted in FIGS. 6 to 9.

Figure 6A:
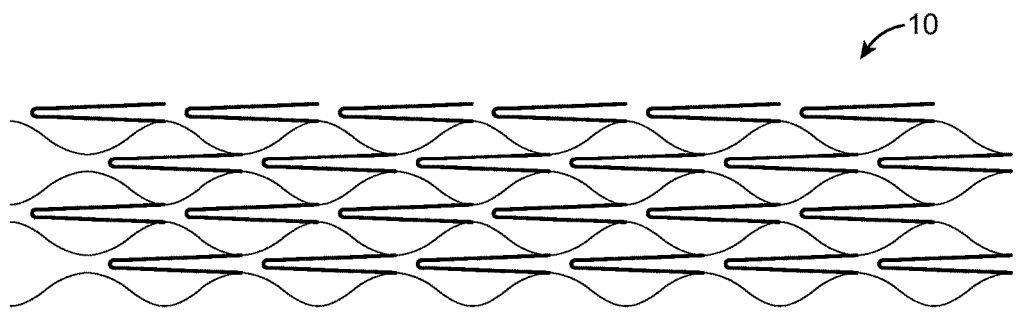
FIGS. 6A and 6B are side views of another stent, in respective radially contracted (FIG. 6A) and radially expanded (FIG. 6B) states, where the stent has been cut open along its longitudinal axis and laid out in a plane.
Figure 6B:
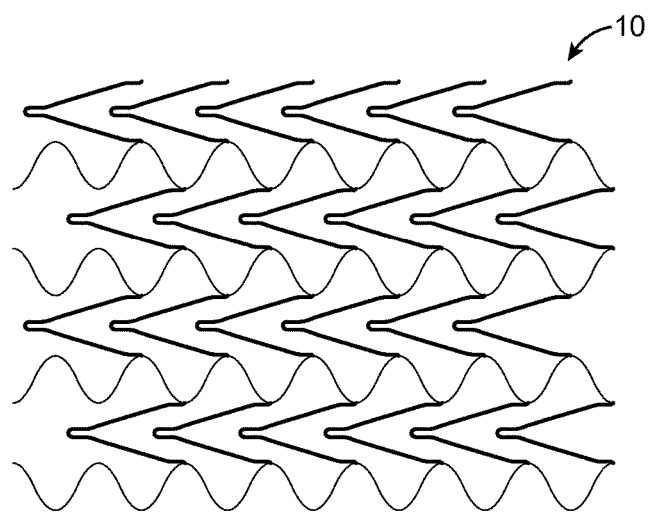

FIGS. 6A and 6B are side views of a stent 10 according to another embodiment. In FIGS. 6A and 6B, the stent 10 has been cut open along its longitudinal axis and laid out in a plane. The stent 10 depicted in FIGS. 6A and 6B includes a plurality of radially expandable circumferential segments, and axially expandable connecting members connecting adjacent circumferential segments of the plurality. The stent 10 has a delivery, axially expanded configuration (FIG. 6A) in which the connecting members are expanded axially, and an axial distance between adjacent circumferential segments of the plurality is greater than when the stent 10 is in its relaxed configuration (described below). The stent 10 also has a relaxed, axially contracted configuration (FIG. 6B) in which the connecting members are contracted axially and each circumferential segment is nested with at least one adjacent circumferential segment. The elongate elements in the stent 10 depicted in FIGS. 6A and 6B have different widths.

Figure 7A:
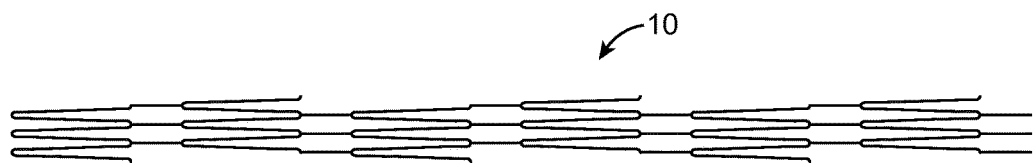
FIGS. 7A and 7B are side views of yet another stent, in respective radially contracted (FIG. 7A) and radially expanded (FIG. 7B) states, where the stent has been cut open along its longitudinal axis and laid out in a plane.
Figure 7B:
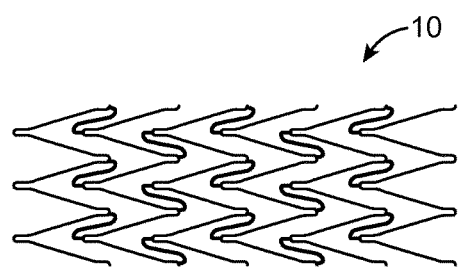

FIGS. 7A and 7B are side views of a stent 10 according to still another embodiment. In FIGS. 7A and 7B, the stent 10 has been cut open along its longitudinal axis and laid out in a plane. The stent 10 depicted in FIGS. 7A and 7B includes a plurality of radially expandable circumferential segments, and axially expandable connecting members connecting adjacent circumferential segments of the plurality. The stent 10 has a delivery, axially expanded configuration (FIG. 7A) in which the connecting members are linearly shaped, and an axial distance between adjacent circumferential segments of the plurality is greater than when the stent 10 is in its relaxed configuration (described below). The stent 10 also has a relaxed, axially contracted configuration (FIG. 7B) in which the connecting members are "S" shaped, and each circumferential segment is nested with at least one adjacent circumferential segment.

Figure 8:
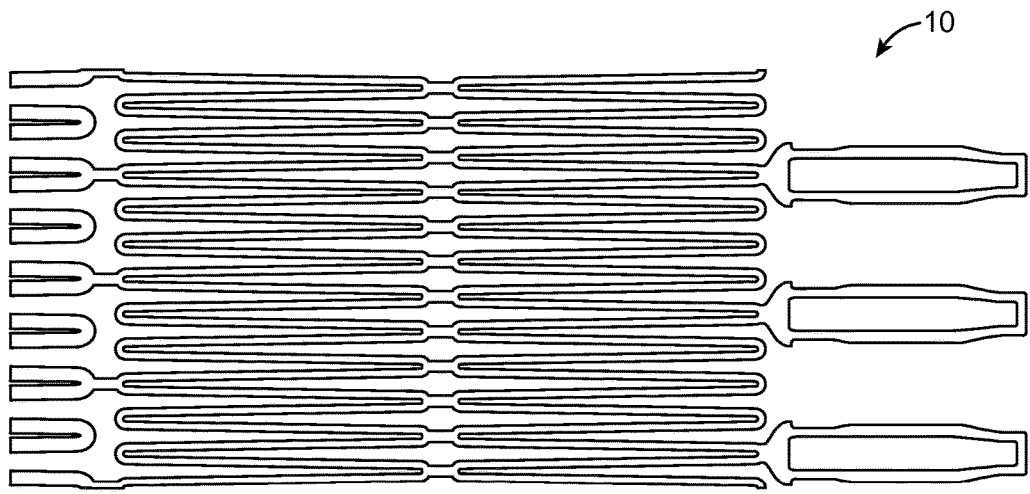
FIG. 8 is a side view of still another stent, in respective radially contracted state, where the stent has been cut open along its longitudinal axis and laid out in a plane.

FIG. 8 is a side view of a stent 10 according to yet another embodiment. In FIG. 8, the stent 10 has been cut open along its longitudinal axis and laid out in a plane. The stent 10 design depicted in FIG. 8 imparts increased axial stiffness at the outer edges of the stent 10 to facilitate loading into a delivery catheter. The elongate elements in the stent 10 depicted in FIG. 8 have different widths and form a complicated pattern.

Figure 9A:
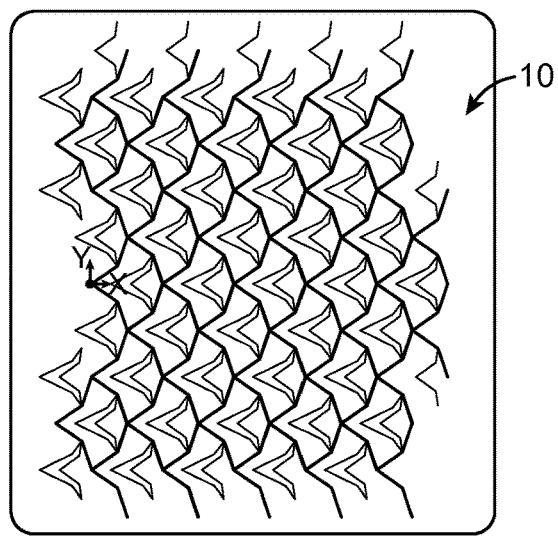
FIGS. 9A, 9B and 9C are side views of yet another stent, in respective radially contracted (FIG. 9B) and radially expanded (FIGS. 9A and 9C) states, where the stent has been cut open along its longitudinal axis and laid out in a plane.
Figure 9B:
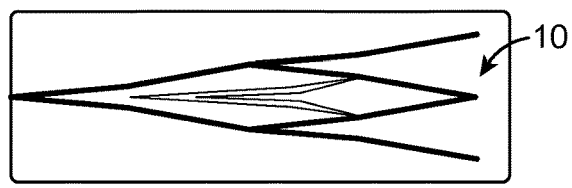
Figure 9C:
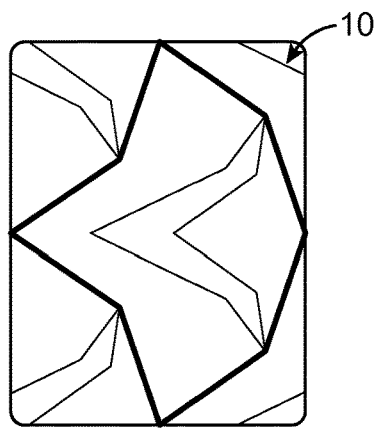

FIGS. 9A, 9B and 9C are side views of a stent 10 according to still another embodiment. In FIGS. 9A, 9B and 9C, the stent 10 has been cut open along its longitudinal axis and laid out in a plane. In FIG. 9B, the stent 10 is in its delivery configuration. In FIGS. 9A and 9C, the stent 10 is in its relaxed configuration. The stent design depicted in FIGS. 9A, 9B and 9C imparts provides more stent material per area of stent and resheathability. The elongate elements in the stent 10 depicted in FIGS. 9A, 9B and 9C have different widths and form a complicated pattern.

A method of delivering a stent, and a stent delivery system for practicing the method will now be described with reference to FIGS. 10A, 10B, 11A and 11B. The target site in the method is typically a neurovascular site, such as a site 54 in the brain, which is accessible only via a tortuous vascular path 56. Tortuous vascular paths 56 contain a plurality of bends or turns which may be greater than 90° turns, and involve vessels which are less than about 8 mm, and as small as 2 mm to 3 mm, in diameter.

Figure 10A:
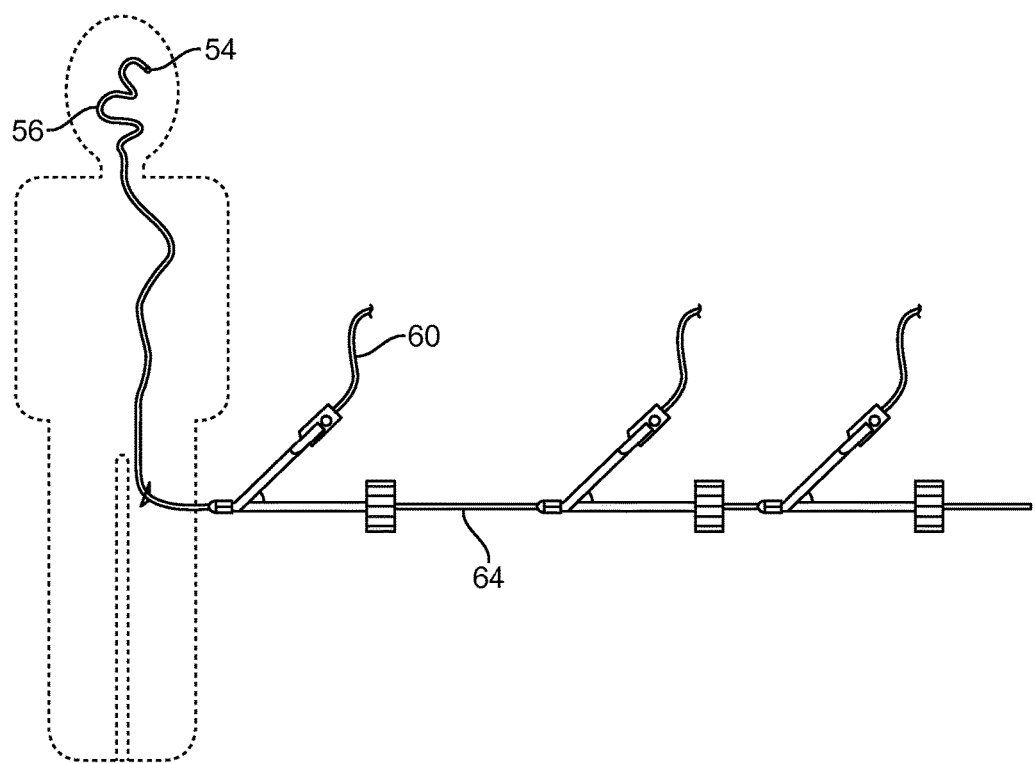
FIGS. 10A and 10B are schematic views of various components of a stent-delivery system at two stages of a stent-delivery method.

Initially, a guide catheter 60 is placed at the target site 54 according to known methods. Then the target site 54 is accessed by a flexible guidewire (such as described in U.S. Pat. No. 4,619,274) and a flexible catheter 64, as shown in FIG. 10A. Once the target site 54 is reached by the flexible guidewire and flexible catheter 64, the flexible catheter 64 is pulled out over the guidewire, leaving the flexible guidewire in place. The stent-delivery catheter 62, as seen in FIG. 10B, is advanced over the guidewire until the target site 54 is reached.

Figure 11A:
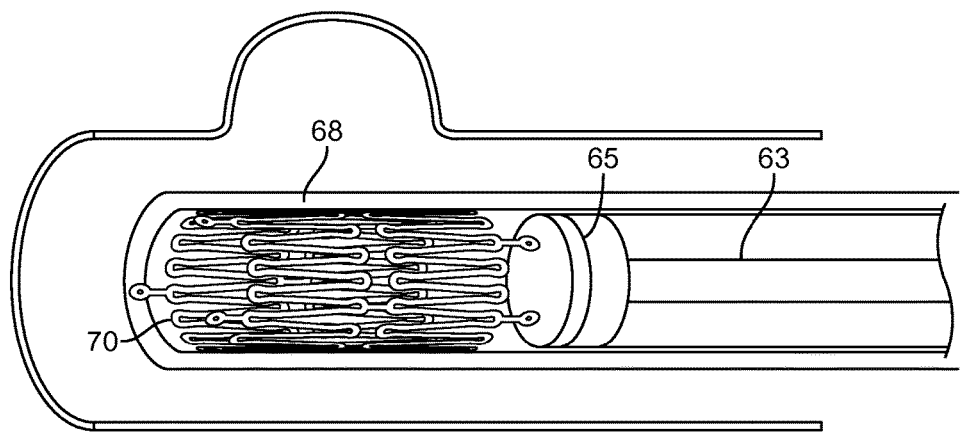
FIGS. 11A and 11B are detailed schematic views of the distal end portion of a stent-delivery system. The distal end portion is shown deployed in a vessel adjacent a vascular target site, just prior to release at the target site (FIG. 11A) and after deployment at the site and stent expansion in the vessel (FIG. 11B).

The distal end of stent-delivery catheter 62 is shown in FIG. 11A, and includes a catheter distal end 68 having an inner lumen having a diameter between about 0.5 mm to about 2 mm, and preferably between about 0.71 mm to about 1.65 mm. A stent 70 is carried in its contracted state at the distal end 68 of the catheter 62.

Figure 10B:
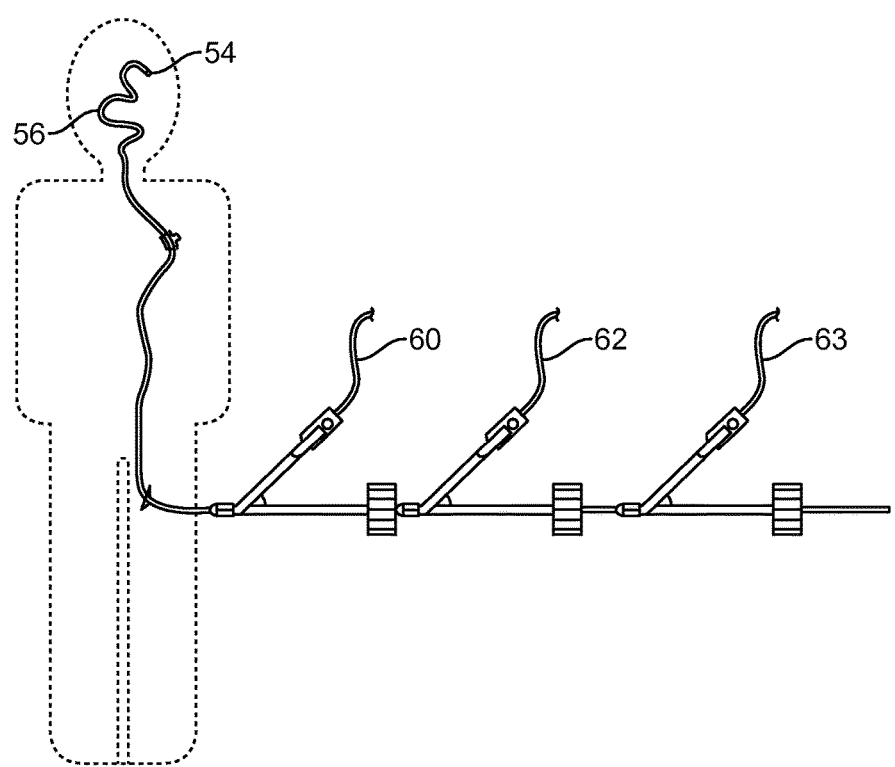
Figure 11B:
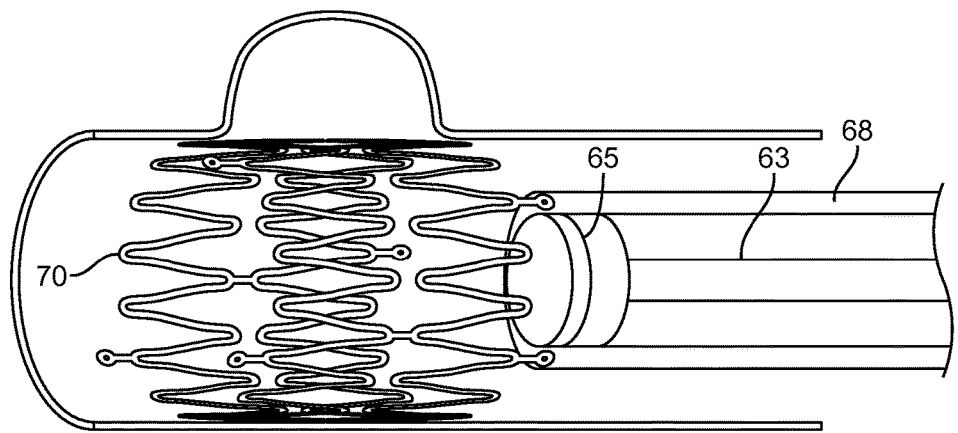

Once the stent-delivery catheter 62 is in place with its distal end 68 at the target site, the guidewire is removed and replaced with a pusher wire 63 (as shown in FIG. 10B) having a distal-end stabilizer or "bumper" 65, which has a distal head surface dimensioned to engage the proximal end of the stent 70. To deploy the stent 70, the pusher wire 63 is advanced and pushed against the stent 70 until the stent 70 is pushed out of the catheter 62, as shown in FIG. 11B. Once released from the constraints of the catheter 62, the stent 70 is free to self-expand to a diameter slightly greater than the diameter of the vascular site, thus anchoring (via an interference fit) the stent 70 in place at the target site.

The stent delivery system used in the above-described method includes a guidewire, a stent-delivery catheter 62 having a lumen inner diameter of 0.5 mm to 2 mm and a distal end region 68 adapted to carry a stent 70 therein in its contracted state, and a pusher wire 63. The catheter 62 and stent 70 are adapted to be moved axially along the guide wire for placing the stent 70 at the target site. The pusher wire 63 is movable through the catheter 62 for forcing the stent 70 out of the catheter 62 into the vascular site, where stent radial expansion to its expanded state is effective to anchor the stent at the target site.

Figure 12:
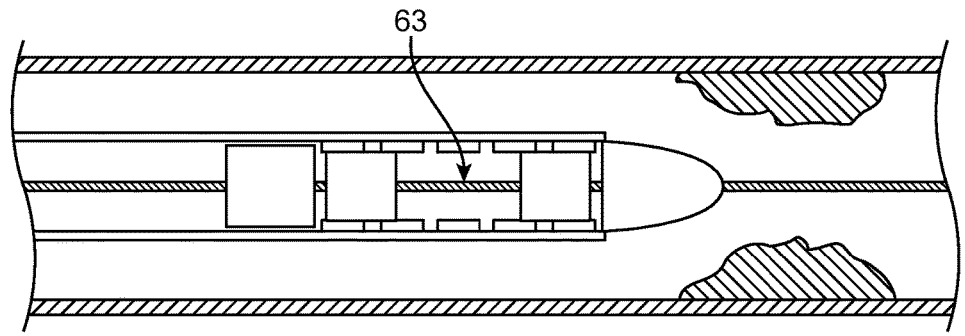
FIG. 12 is a schematic view of various components of another stent-delivery system.

While the stent pusher wire 63 depicted in FIGS. 11A and 11B includes only one bumper at its distal end, other stent pusher wires are more complicated. For instance, the stent pusher wire 63 depicted in FIG. 12 includes bumpers proximal of, distal of and underlying the stent. Such bumpers increase the control of stent movement during delivery. While the stent pusher wires 63 depicted in FIGS. 11A, 11B and 12 have bumpers. Other stent pusher wires may include balloons configured to expand and deploy stents mounted thereon.

The stent and system employing the stent of the present invention can be used in the treatment of a variety of vascular lesions such as an aneurysm, fistula, occlusion, or narrowing and is particularly useful in treating targets located in tortuous and narrow vessels, for example in the neurovascular system, or in certain sites within the coronary vascular system, or in sites within the peripheral vascular system such as superficial femoral, popliteal, or renal arteries.

The axial construction of the stent, composed of short tubular members joined by axial connections, and the ability of the joined members to flex radially, by distributed bending within the looped regions of the wire elements, allows the stent to be moved over high-angle, small-radius bends, with relatively little localized stress and metal fatigue.

The ability of the stent to be close-packed, in its contracted state, and have a smooth wave-like character in its expanded (and expanding) state, allows the stent to expand several fold when deployed, with a minimum risk of metal fatigue due to concentrated stresses, or damage to the vessel wall, due to sharp points on the stent. In its expanded state, the stent provides good radial strength, for holding the stent in place.

The stent has a low overall profile, which may be in the about 0.014"-about 0.050" range with the stent in its contracted state. Finally, the stent can provide an open-network skeleton that allows for delivery of additional agents, e.g., vaso-occlusive coils, through the stent into the underlying aneurysm cavity.

A preferred method of manufacturing stents such as those described above is to cut the stent from a thin-walled tubular member. An exemplary tubular member can be made from stainless steel. Cutting the tubular member removes unwanted portions of the tubular member to create opening to form the stent pattern. Accurately cutting the tubular member allows the portions of the tubular member that will form the stent to have a finer structure, which, in turn, increases stent design options. An exemplary method of cutting the tubular member using a computer-controlled laser is depicted in FIG. 13.

The tubing from which the stent is to be cut may be made of a suitable biocompatible material, such as stainless steel, nitinol, or other metals and polymers. Stents having complex shapes are cut from tubes that having outer diameters that are approximately the same as the outer diameters as the vessels into which they are to be implanted. A typical stent has an outer diameter of about 1.5 mm (up to about 5 mm) in the unexpanded condition, and can be expanded to an outer diameter of about 2.5 mm or more. Accordingly, the tubing from which the stent is made must have an outer diameter of about 1.5 mm (up to about 5 mm; the same as the unexpanded stent). A typical stent wall thickness (and tubing wall thickness) is about 0.075 mm. Thin-walled stents having larger diameters need more support during laser cutting compares to thicker-walled stents or stents having smaller diameters.

Figure 13:
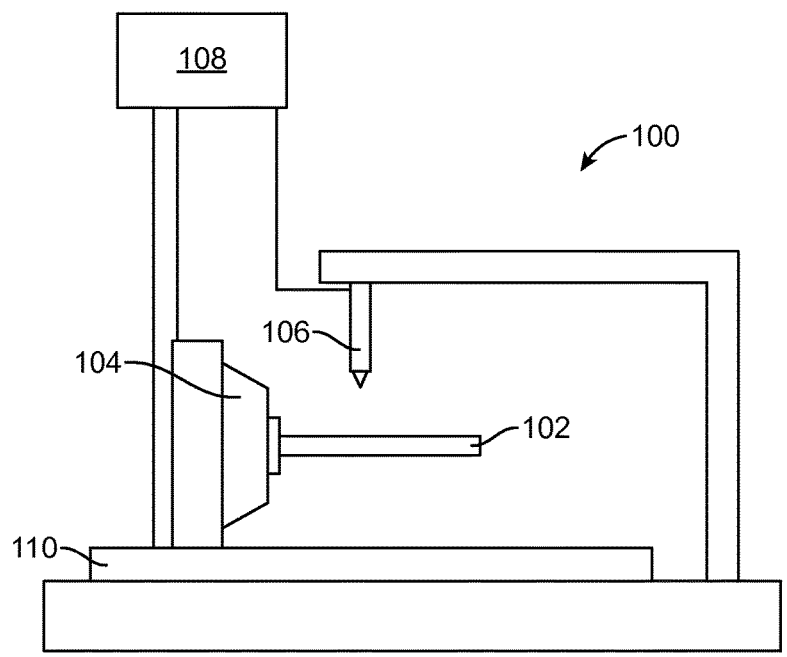
FIGS. 13 and 14 are schematic views of two prior art stent cutting systems.

FIG. 13 depicts an existing computer-controlled system 100 configured to cut a stent from a tubular member 102. The tubular member 102 is mounted on a computer numerical controlled ("CNC") collet (i.e., a "chuck") 104 adjacent a laser 106. The CNC collet 104 and the laser 106 are controlled by a computer 108 using software containing coded alphanumeric data, in order to rotate the tubular member 102 relative to a laser 106 and to activate the laser 106 at appropriate times. The appropriate time to active the laser 106 is typically when a portion of the tubular member 102 to be removed is positioned in the path of the laser's beam 114 (see FIGS. 15 and 16). The CNC collet 104 is configured to rotate the tubular member 102 about its longitudinal axis in order to provide the laser 106 access to the entire outer surface of the tubular member 102 in a ring around the longitudinal axis of the tubular member 102. In some existing stent cutting systems (not shown), one end of the tubular member is mounted on a collet and the other end of the tubular member is mounted on an opposing collet for improved stability during stent cutting.

In the embodiment depicted in FIG. 13, the CNC collet 104 and the tubular member 102 mounted thereon are disposed on and fixed to a controllably-movable support structures such as a CNC table 110. The CNC table 110 is controlled by the computer 108 using software containing coded alphanumeric data, in order to positioning the tubular member 100 relative to the laser 106. The CNC table 110 is movable along X and Y axes, which are perpendicular to each other and approximately orthogonal to the axis of the laser 106. In other embodiments, the CNC table 110 may be movable along other axes. A combination of rotation of the CNC collet 104 and movement of the CNC table 110, both under control of the computer 108, can present any surface of the tubular member 102 to the laser 106. In this embodiment, the laser 106 is stationary, however in other embodiments, the laser may also be movable under control of the computer 108. While the collet 104, laser 106 and table 110 are all described as controlled by a computer 108, they can be controlled by a network of interconnected computers 108.

The tubular member 100 is rotated and moved in an X-Y plane orthogonal to the axis of the laser 106, which is also under control of the computer 108. Under computer 108 control, the laser 106 selectively removes unwanted material from any surface of the tubular member 102 by ablation and a pattern is cut into the tubular member 102. The tubular member 102 is therefore cut into the discrete pattern of the finished stent. After the tubular member 102 is cut to form the finished stent, debris from laser cutting can be removed (e.g., mechanically or chemically) and the finished stent can be electropolished.

The process of cutting a stent pattern from a tubular member 102 can be automated except for loading and unloading the tubular member 102. Referring again to FIG. 13, the tubular member 102 may be presented to and moved relative to the laser 106 using the CNC collet 104 for axial rotation of the tubular member 102, and the CNC table 110 to move the tubular member relative to the laser 106, all controlled by the computer 108, as described above. The entire tubular member 102 can be cut to form a stent pattern using the computer-controlled laser 106 described above. The CNC software in the computer 108 is customizable for the particular configuration of the system parts used (including the tubular member 102) and the pattern to be cut into the tubular member 102.

Figure 14:
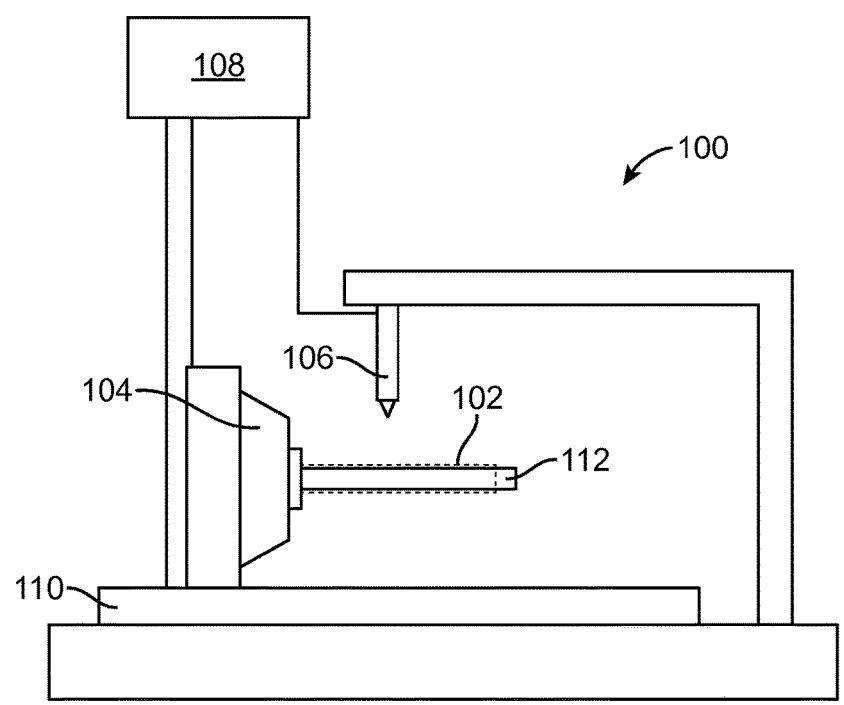

Existing laser stent cutting systems directly mount the tubular member 102 on the CNC collet 104 (see FIG. 13). In some existing system, a mandrel 112 can also be inserted into the tubular member 102, and the tubular member 102 and/or the mandrel 112 can be mounted on the CNC collet 104, as shown in FIG. 14. The tubular member 102 is shown in phantom in FIG. 14 to enable visualization of the mandrel 112.

Figure 15:
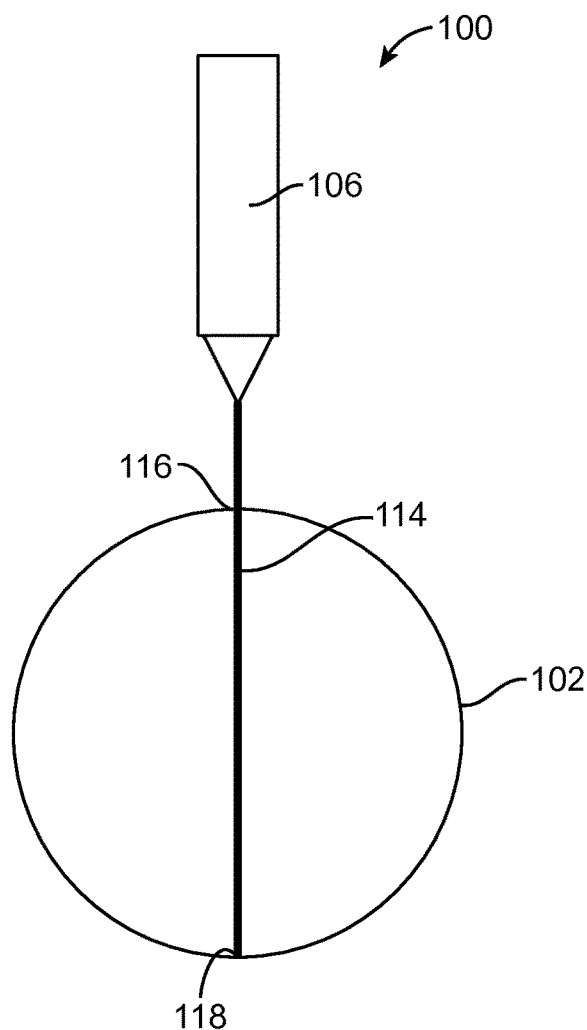
FIGS. 15, 16 and 17 are (detailed, cross-sectional) schematic views through portions of three prior art stent cutting systems.
Figure 16:
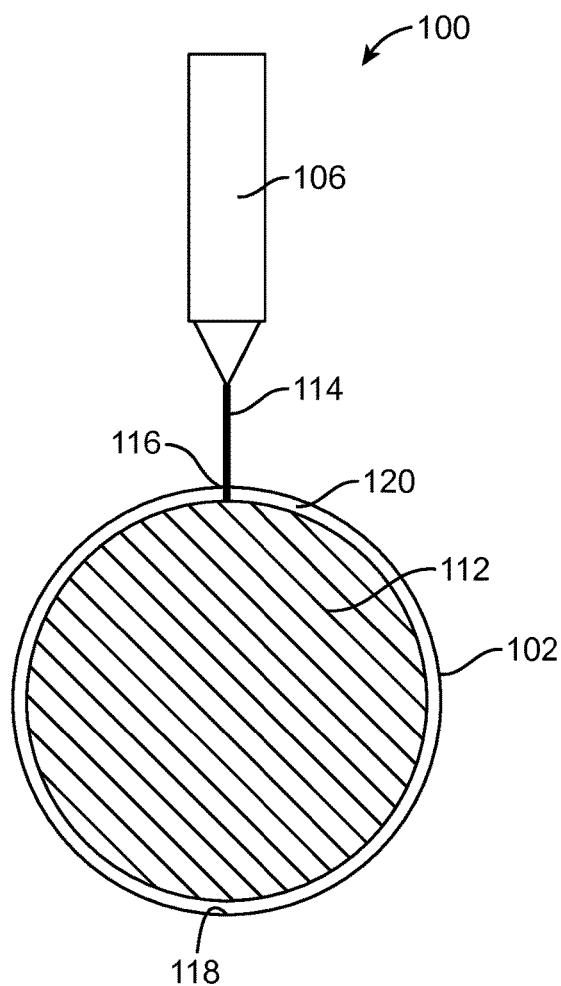
Figure 17:
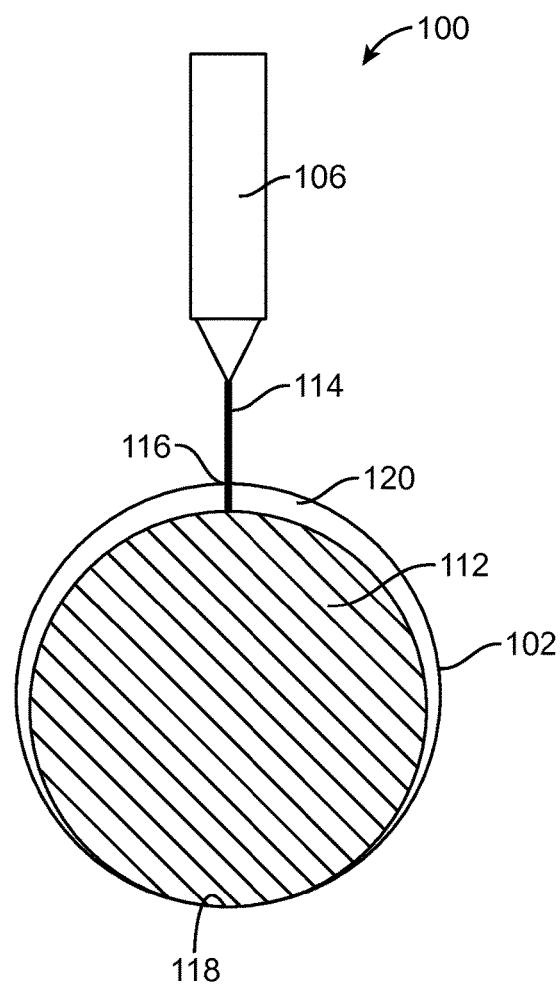

In stent cutting systems that do not use a mandrel, a beam 114 from the laser 106 can cut through the first side 116 of the tubular member 102, which is closest to the laser 106, and affect (e.g., damage or cut through) the second side 118 of the tubular member 102 opposite of the first side 116, as shown in cross-section in FIG. 15. The mandrels 112 in the embodiments depicted in FIGS. 16 and 17 prevent the beam 114 from affecting the second side 118 of the tubular member 102 by blocking the beam 114 after it has cut through the intended target in the first side 116 of the tubular member 102. In FIG. 16, the tubular member 102 and the mandrel 112 are mounted on the collet (not shown). Therefore, the tubular member 102 and the mandrel 112 are approximately coaxial. In FIG. 17, only the tubular member 102 is mounted on the collet (not shown), and the mandrel 112 is supported by the mounted tubular member 102. Therefore, the mandrel 112 rests on the bottom (i.e., the second side 118) of the tubular member 102. Both of the arrangements depicted in FIGS. 16 and 17 result in a space 120 between tubular member 102 and the mandrel 112. In FIG. 16, the space 120 is approximately annular. In FIG. 17, the space 120 is a narrow crescent.

Existing mandrels 112 for use with stent cutting systems 100 have outer diameters that are less that the inner diameters of the tubular members 102 used therewith. This facilitates insertion into and removal from the tubular members 102 before and after cutting the stent form the tubular member 102, respectively. However, because of the space 120 between the tubular member 102 and the mandrel 112, existing mandrels 112 do not significantly improve the stability of the tubular member 102 during stent cutting.

Another problem of existing stent cutting systems is that they generate a residue of melted and re-solidified material (known as "slag") along the edges of the cut tubular member 102. This slag residue becomes rough and uneven deposits on the surfaces or edges of the stent struts, particularly on the inner surfaces and edges of the stent. A portion of the slag deposits and residue from the cutting procedure may be removed with a light scouring, scraping or abrading procedure. However, even after such scraping, some slag deposits remain, leaving burrs, cracks, pitting and/or surface unevenness in the stent. Using a mandrel 112 with the stent cutting system 100, as shown in FIGS. 16 and 17, reduces the splattering and slag formation on the stent, but some slag is still formed while cutting the stent from the tubular member 102.

In the disclosed embodiments of stent cutting systems 200, the mandrels 212 are configured to support the tubular member 202 during stent cutting to reduce vibration, sagging and other types of movement of the tubular member 202 during stent cutting. Vibration, sagging and tubular member movement are especially problematic in stent cutting systems where only one end of the tubular member is supported. A sagging tubular member 202 can change the relative location of point of focus of the laser 206 along the longitudinal axis of the tubular member 202. Reducing vibration, sagging and movement of the tubular member 202 during stent cutting increases both the accuracy (i.e., closeness to the desired cutting location) and precision (i.e., repeatability) of stent cutting. Therefore, the disclosed stent cutting systems 200 enable accurate and precise cutting of stent designs with smaller strut widths (e.g., approximately 0.075 mm).

Figure 18:
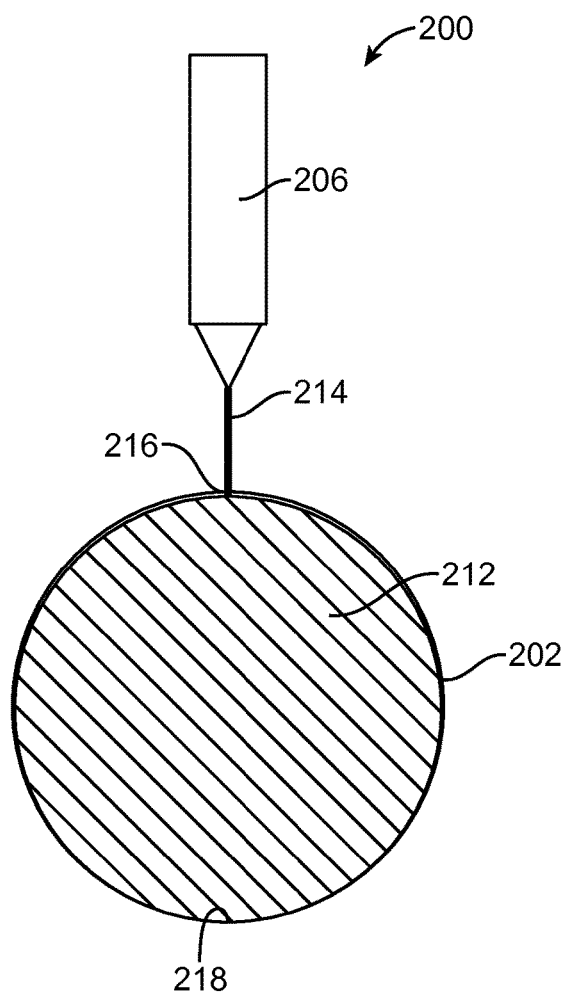
FIG. 18 is a (detailed, cross-sectional) schematic view through portions of a stent cutting system according to one embodiment.

In the embodiment depicted in FIG. 18, the outer diameter of the mandrel 212 is approximately equal to the inner diameter of the tubular member 202. While FIG. 18 may appear to include a space between the outer surface of the mandrel 212 and the inner surface of the tubular member 202, this is a limitation of the medium. The mandrel 212 substantially fills the lumen of the tubular member 202. The mandrel 212 is rigid and maintains substantially intimate contact with the tubular member 202 as it is being cut to form the stent. The mandrel 212 preferably adheres to the inner surface of the tubular member 202. Accordingly, the mandrel 212 provides structural support to the tubular member 202, increasing its longitudinal stiffness and rigidity. Further, the mandrel 212 substantially fills the lumen of the tubular member 202 to further increase its longitudinal stiffness and rigidity.

In addition to blocking the beam 214 of the laser 216 from affecting the opposite side 218 of the tubular member 202, the mandrel 212 also minimizes movement of the tubular member 202 during stent cutting by providing structural support. Tubular member 202 movement is reduced regardless of whether the tubular member 202 and/or the mandrel 212 are mounted on the collet (not shown), and whether one or both ends of the tubular member 202 and/or the mandrel 212 are supported by the collet (not shown).

Filling the lumen of the tubular member 202 with the mandrel 212 also minimizes slag formation during stent cutting because it eliminates splattering. Slag formation is further reduced by using an ultra-short-pulse laser, which limits the area affected by the laser (the area of focus). As a result, the solid material forming the tubular member 202 is converted directly to vapor (vaporized) and little to no slag is formed. Moreover, using an ultra-short-pulse laser reduces the size of the heat-affected zone (described below).

The mandrel 212 can be made from a thermally and dimensionally stable material, such as glass-filled acrylonitrile butadiene styrene ("ABS") or a thermoplastic polymer sold under the trade name Crystalbond™ 509 by Ted Pella, Inc. of Redding, Calif. Using a thermally stable material minimizes thermal expansion caused by the heat of the laser. Such thermal expansion is counterproductive to accurate and precise stent cutting because an expanding mandrel 212 would move the tubular member 202. Other suitable thermally and dimensionally stable materials include non-crystalline plastics and resins, filled structures (e.g., polymers doped with carbon black, silica or glass beads to improve dimensional stability), and preformed structures (e.g., woven carbon fibers impregnated with a thermoset or thermoplastic polymer). Suitable carbon fibers include carbon nanotubes, graphene tubes, fiberglass and carbon fiber. Woven or braided pre-impregnated structures can be expanded into intimate contact with the inner surface of the tubular member 202 before stent cutting (described below).

Figure 19:
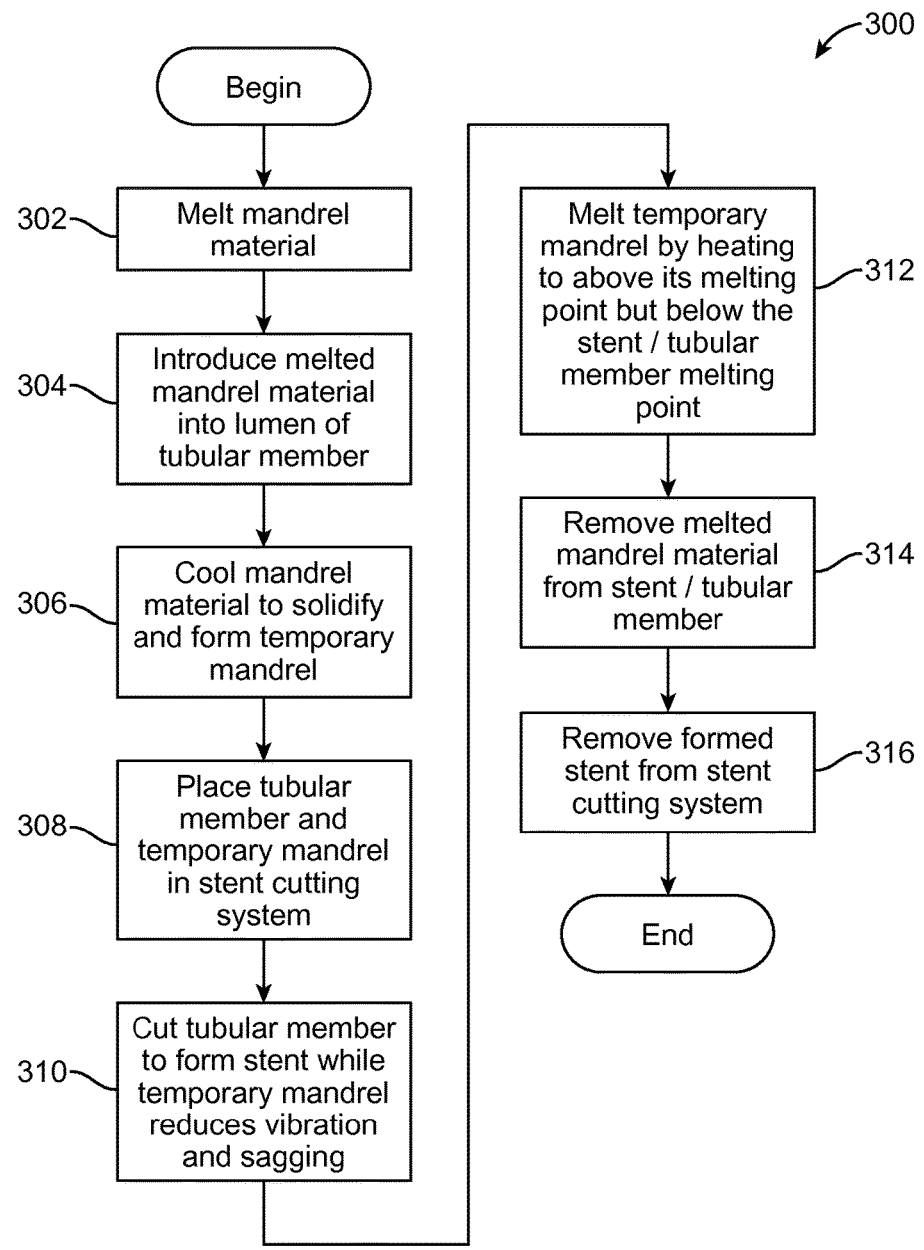
FIGS. 19 and 20 are flow charts showing methods of cutting a stent from a tubular member according to two embodiments.

FIG. 19 depicts a method 300 of laser cutting a stent from a tubular member 202 using the above described stent cutting system 200. In the method 300, a temporary mandrel 212 is formed from a mandrel material having a lower melting point than the tubular member material forming the tubular member 202. A suitable mandrel 212 material for this method 300 is a thermoplastic polymer such as ABS, glass-filled ABS and Crystalbond™ 509.

In step 302, the mandrel material is melted by raising the temperature of the mandrel material above its melting point. In step 304, the melted mandrel material is introduced into the lumen of the tubular member 202, for instance, under pressure (i.e., injected) or by gravity (i.e., poured). In step 306, the mandrel material is cooled below its melting point and allowed to anneal/solidify to form the temporary mandrel 212, which increases the longitudinal stiffness and rigidity of the tubular member 202. The cooling step is performed slowly to reduce residual internal stresses that may form in the temporary mandrel 212 during cooling, which may warp the tubular member 202 during cutting. In a preferred embodiment, the solidified temporary mandrel 212 adheres to the inner surface of the tubular member 202 due to the tackiness of the mandrel material. This adhesion further increases the stiffness and rigidity, by minimizing the number and size of microscopic spaces between the tubular member 202 and the temporary mandrel 212. The temporary mandrel 212 can be formed with or without a mandrel lumen (by using a rod to form the mandrel lumen during the mandrel molding process). A hollow temporary mandrel 212 will be easier to remove (described below) from the formed stent.

In step 308, the tubular member 202 and the temporary mandrel 212 contained therein are placed in the stent cutting system 200 as described above. In step 310, the tubular member 202 is laser cut to form the stent using the systems and methods described above. Because the thermally and dimensionally stable temporary mandrel 212 has been positioned in the lumen of the tubular member 202, vibration and sagging of the tubular member 212 during stent cutting is reduced. This in turn increases the accuracy and precisions with which the tubular member 212 can be cut, enabling stent designs with finer details (e.g., smaller strut widths).

After the tubular member 202 is cut to form the stent, the temporary mandrel 212 is removed in step 312 by increasing the temperature of the combined stent/tubular member 202 and temporary mandrel 212 to above the melting point of the temporary mandrel 212, but below the melting point of the stent/tubular member 202. The heat melts the thermoplastic polymer material forming the temporary mandrel 212, but does not significantly affect the stent/tubular member 202. In step 314, the melted material is removed from the stent/tubular member 202 by gravity, with a solvent (e.g., heated acetone, water or methanol) and/or with vibration or other mechanical means. Finally, the completely formed stent is removed from the system 200 in step 316.

Figure 20:
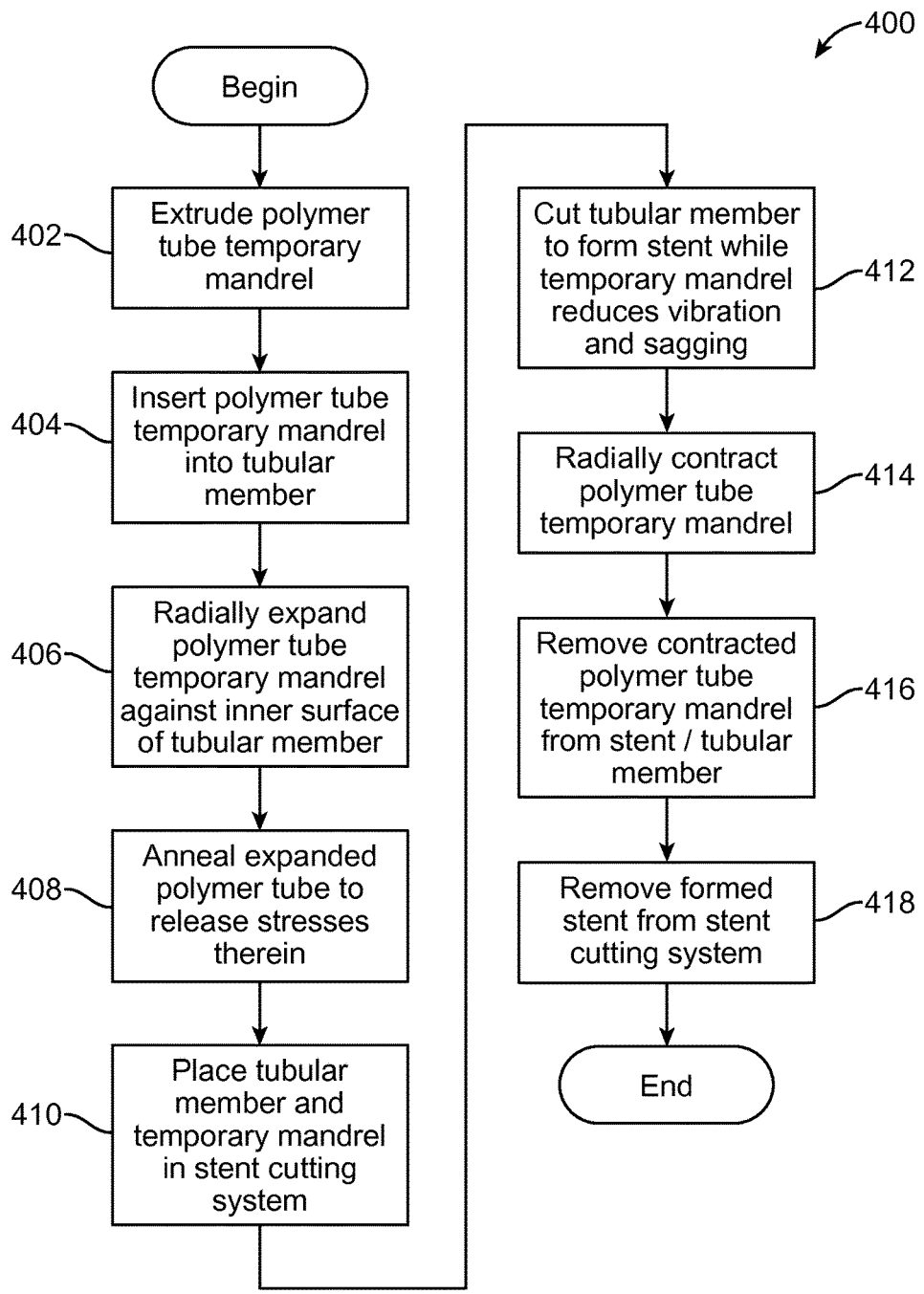
Figures 21, 22:
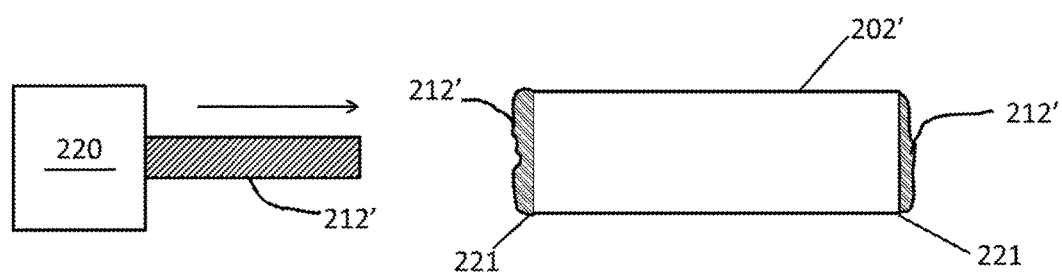
FIG. 21 is a (detailed) schematic depiction of an extrusion of a polymer member suitable for use as mandrel for supporting a tube during laser cutting, in accordance with one embodiment.
FIG. 22 is a side perspective view of a tube to be laser cut, in which the polymer member depicted in FIG. 21 has been positioned within a lumen of the tube.

In another method 400 of laser cutting a stent from a tubular member 202' using the above described stent cutting system 200, a temporary mandrel 212' is formed by polymer extrusion, as depicted in FIG. 20. A suitable mandrel material for this method 400 is a thermoplastic polymer, as described above with respect to method 300. In step 402, a polymer tube temporary mandrel 212' is extruded using a known extrusion apparatus 220, as shown in FIG. 21. In step 404, the polymer (or pre-polymer) tube temporary mandrel 212' is inserted into the lumen 221 of the tubular member 202' to be laser cut, as shown in FIG. 22. For thermosetting polymers, the "polymer' is a partially reacted pre-polymer, and the heat cure forms the final polymer by reaction of the components with in the pre-polymer mixture. For the purpose describing of this embodiment, the word "polymer" includes these pre-polymers. In step 406, the polymer tube temporary mandrel 212' is radially expanded against the inner luminal surface of the tubular member 202'. The polymer tube temporary mandrel 212' can be plastically expanded by pressurizing the lumen 221 of the polymer tube temporary mandrel 212'. Alternatively, the polymer tube temporary mandrel 212' can be plastically expanded by pressurizing a balloon inserted into the lumen 221 of the polymer tube temporary mandrel 212'.

The expanded polymer tube temporary mandrel 212' increases the longitudinal stiffness and rigidity of the tubular member 202', however excess internal/radial stresses can have undesirable effects during stent cutting. Accordingly, the expanded polymer tube temporary mandrel 212' is annealed in step 408 to reduce the residual internal/radial stresses therein. During a typical annealing step, the polymer tube temporary mandrel 212' is heated to a temperature that allows molecular motion to facilitate the mandrel 212' material taking on an isotropic form. However, the polymer tube temporary mandrel 212' is not heated to or above its melting point. Then the polymer tube temporary mandrel 212' is cooled or allowed to cool. In a preferred embodiment, the expanded polymer tube temporary mandrel 212' adheres to the inner surface of the tubular member 202', due to the tackiness of the polymer from which it is extruded. This adhesion further increases the stiffness and rigidity, by minimizing the number and size of microscopic spaces between the tubular member 202' and the temporary mandrel 212'.

Figure 23:
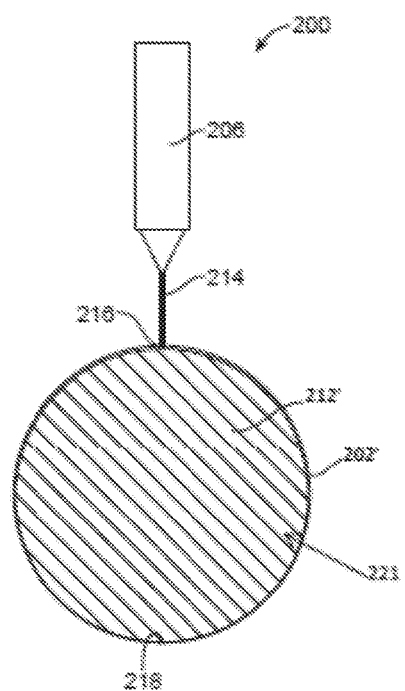
FIG. 23 is a (detailed, cross-sectional) schematic view through a portion of a stent cutting system according to the embodiment of FIGS. 20-23.

In step 410, and with additional reference to FIG. 23, the tubular member 202' and the temporary mandrel 212' contained therein are placed in the stent cutting system 200 as described above. In step 412, the tubular member 202' is laser cut to form the stent using the systems and methods described above. Because the thermally and dimensionally stable temporary mandrel 212' has been radially expanded in the lumen of the tubular member 202', vibration and sagging of the tubular member 212' during stent cutting is reduced. This in turn increases the accuracy and precisions with which the tubular member 212' can be cut, enabling stent designs with finer details (e.g., smaller strut widths).

After the tubular member 202' is cut to form the stent, the polymer tube temporary mandrel 212' is removed by first radially contracting it in step 414. The radius of the extruded tube temporary mandrel 212' can be reduced by stretching the extruded tube temporary mandrel 212' along its longitudinal axis. The stretching can be facilitated by raising the temperature of the mandrel to allow the mandrel material to stretch more easily. In step 416, the radially contracted polymer tube temporary mandrel 212' is removed from the stent/tubular member 202'. Finally, the completely formed stent is removed from the system 200 in step 418. Alternatively, the polymer tube temporary mandrel 212' can be removed from the stent/tubular member 202' by dissolving it in a solvent or melting it with heat.

While the method 400 depicted in FIG. 20 includes extruding a polymer tube temporary mandrel 212, tubular temporary mandrels 212 can be formed by other methods (in step 402) without significantly altering the other steps in method 400. One such alternative method is to weave a tubular braid from carbon fibers including carbon nanotubes, graphene tubes, fiberglass and carbon fiber, and impregnating the tubular braid with a thermoset polymer, (e.g., epoxy, bismaleimide ("BMI") or phenolic resins) or thermoplastic polymer (e.g., acrylonitrile butadiene styrene ("ABS"), polyethylene terephthalate ("PET"), polyethylene ("PE"), polyphenylene sulfide ("PPS") or polyether ether ketone ("PEEK")). The pre-impregnated braided tubular temporary mandrel 212 can be expanded into intimate contact with the inner surface of the tubular member 202 with heat and pressure as described above with respect to method 400. The expanded pre-impregnated braided tubular temporary mandrel 212 can be cured in an expanded condition in the tubular member 202 by adjusting its temperature depending on the material from which it is made. Thermoset polymers are heat cured and thermoplastic polymers are heat formed and cooled to cure (as described above). The expanded pre-impregnated braided tubular temporary mandrel 212 can be removed from the formed stent/tubular member 202 by heating and axial loading to stretch out and reduce the diameter of the assembly, or by dissolving the matrix material of the temporary mandrel 212 in a solvent. The remainder of the stent cutting method steps are substantially the same as those of the method 400 depicted in FIG. 20.

Another alternative method forms the tubular temporary mandrel 212 by drawing one slug (or co-drawing multiple slugs) through an annular die to form a drawn (or co-drawn) tubular temporary mandrel 212. The remainder of the stent cutting method steps are substantially the same as those of the method 400 depicted in FIG. 20.

In still another alternative stent cutting method, a tubular temporary mandrel 212 is made by first filling the lumen of the tubular member 202 with a mixture of a polymer and a solvent. Then the tubular member 202 is rotated as the solvent is evaporated to produce a tubular temporary mandrel 212. The remainder of the stent cutting method steps are substantially the same as those of the method 400 depicted in FIG. 20.

In yet another alternative stent cutting method, a composite temporary mandrel 212 is made by first inserting rigid rods into the lumen of the tubular member 202, then filling the space between the rigid rods with melted mandrel material as described in the method 300 depicted in FIG. 19. The remainder of the stent cutting method steps are substantially the same as those of the method 300 depicted in FIG. 19.

In another alternative stent cutting method, a solid temporary mandrel 212 is made by first inserting a preformed polymer rod into the lumen of the tubular member 202, then melting the polymer rod and axially compressing the melted polymer while it is setting to release the inherent stress. For the purpose describing of this embodiment, the word "polymer" includes these pre-polymers, as described above with respect to the embodiment depicted in FIG. 20. The remainder of the stent cutting method steps are substantially the same as those of the method 300 depicted in FIG. 19.

In various other alternative stent cutting methods, the temporary mandrel 212 contained in an outer tubing can be made by forming any of the above-described temporary mandrels 212 in an outer tubing disposed in the lumen of the tubular member 202. The outer tubing can be co-drawn from two or more materials. The outer tubing can also have one or more coatings/films applied to an outer surface thereof. Further, the outer tubing can be cut by the laser and retained in the formed stent to produce a stent with two or more layers.

In various other stent cutting methods, a tie layer can be deposited between any of the above-described temporary mandrels 212 and respective tubular members 202 which they support. Exemplary tie layers may be made from adhesives, which increase the adhesion of the temporary mandrel 212 to the inner surface of the tubular member 202, thereby increasing the rigidity of the temporary mandrel 212/tubular member 202 assembly during stent cutting. The tie layer can be added to either the inner surface of the tubular member 202 or the outer surface of a solid temporary mandrel 212 before the two are assembled. After the tubular member 202 is cut for form a stent, the tie layer may be removed using methods such as those described above for removing a polymer temporary mandrel 212 (e.g., using melting, solvents and mechanical means).

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense.

What is claimed is:

1. A method of manufacturing a tubular medical implant, comprising, in the following order:

inserting an elongate polymer or pre-polymer member into a lumen of an elongate metal tube, the metal tube having an inner wall defining the lumen, wherein the polymer member is hollow and defines a polymer member lumen;

radially expanding the polymer member within the metal tube lumen to thereby increase a frictional force applied by the polymer member against the inner wall of the metal tube, wherein radially expanding the polymer member comprises heating the polymer member and increasing a pressure within the lumen of the heated polymer member;

securing the metal tube, including the expanded polymer member therein, to a collet of a laser etching system;

laser etching a predetermined pattern of openings in the metal tube;

reheating the polymer member;

axially stretching to thereby radially contract the reheated polymer member;

and removing the radially contracted polymer member from the metal tube lumen.

2. The method of manufacturing of claim 1, wherein the polymer member is solid, and wherein radially expanding the polymer member comprises heating the polymer member, and axially compressing the heated polymer member.

3. The method of manufacturing of claim 1, further comprising, after radially expanding the polymer member, and before laser etching the predetermined pattern of openings in the metal tube, annealing the polymer member to reduce or eliminate residual stress stored therein.

4. The method of manufacturing of claim 1, further comprising, prior to inserting the polymer member into the metal tube lumen, applying a tie-layer of adhesive material to one or both of the inner wall of the metal tube and an outer surface of the polymer member.

5. The method of manufacturing of claim 1, wherein inserting the elongate polymer member into the metal tube lumen comprises extruding the polymer member directly into the metal tube lumen.

* * * * *